United States Patent
Paufique

(10) Patent No.: US 7,300,678 B2
(45) Date of Patent: Nov. 27, 2007

(54) METHOD FOR OBTAINING AN ACTIVE PRINCIPLE WITH IMMEDIATE SKIN-TIGHTENING EFFECT AND RESULTING ACTIVE PRINCIPLE

(75) Inventor: Jean-Jacques Paufique, Objat (FR)

(73) Assignee: Societe Industrielle Limousine d'Application Biologique (SILAB), Objat (FR)

( * ) Notice: Subject to any disclaimer, the term of this patent is extended or adjusted under 35 U.S.C. 154(b) by 754 days.

(21) Appl. No.: 10/398,170

(22) PCT Filed: Sep. 27, 2001

(86) PCT No.: PCT/FR01/02995

§ 371 (c)(1),
(2), (4) Date: Oct. 24, 2003

(87) PCT Pub. No.: WO02/28360

PCT Pub. Date: Apr. 11, 2002

(65) Prior Publication Data

US 2004/0052758 A1    Mar. 18, 2004

(30) Foreign Application Priority Data

Oct. 2, 2000 (FR) .................................. 00 12561

(51) Int. Cl.
*A01N 65/00*    (2006.01)
*A61K 8/02*    (2006.01)
*A61K 31/74*    (2006.01)

(52) U.S. Cl. ..................... 424/735; 424/401; 424/78.02

(58) Field of Classification Search ................ 424/401, 424/78.02, 735
See application file for complete search history.

(56) References Cited

FOREIGN PATENT DOCUMENTS

JP    08169816 A  *  7/1996

OTHER PUBLICATIONS

Translation of JP 08169816A.*

* cited by examiner

*Primary Examiner*—Sreeni Padmanabhan
*Assistant Examiner*—Kendra D. Carter
(74) *Attorney, Agent, or Firm*—Young & Thompson

(57) ABSTRACT

The invention concerns an active principle with instant skin-tightening effect useable in cosmetics, the method for obtaining same and compositions comprising said active principle. The source material consists of a white almond press cake.

12 Claims, 1 Drawing Sheet

Figures 1, 2:
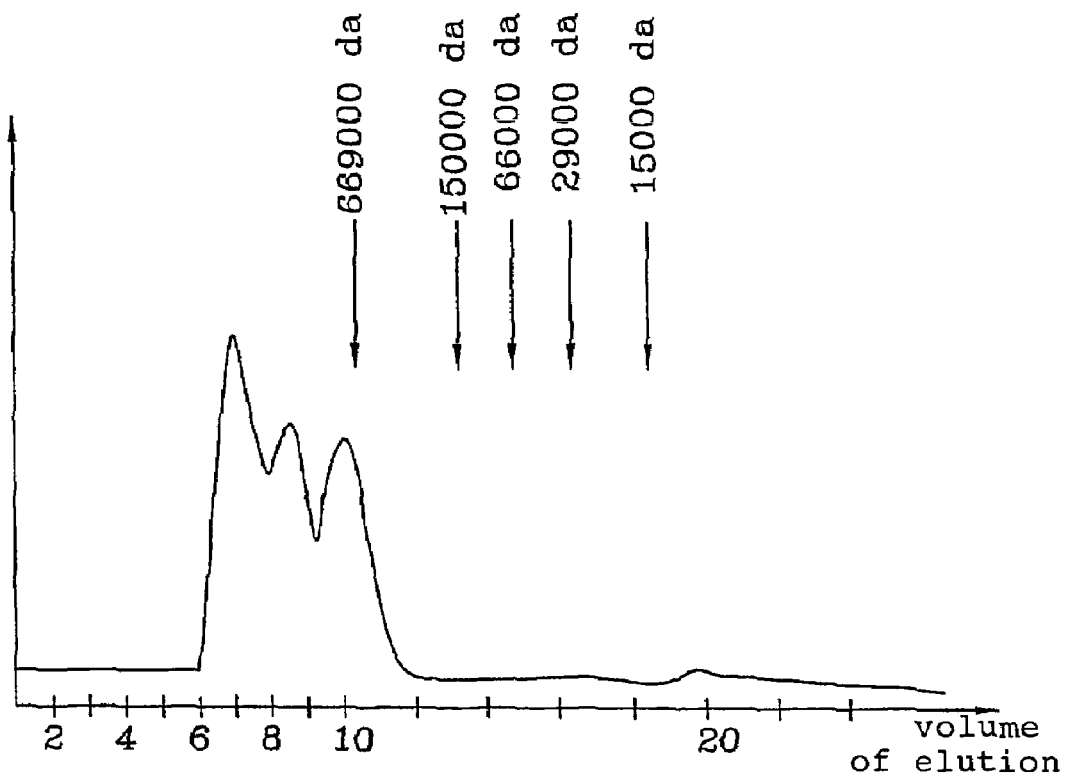

| | Δ % |
|---|---|
| Ue 1% | −6.3 |
| Uf 1% | −5.4 |
| Ue 3% | −9.0 |
| Uf 3% | −9.6 |
| Ue 5% | −12.6 |
| Uf 5% | −14.2 |

METHOD FOR OBTAINING AN ACTIVE PRINCIPLE WITH IMMEDIATE SKIN-TIGHTENING EFFECT AND RESULTING ACTIVE PRINCIPLE

The present invention has for its object an active principle with immediate skin tightening effect, made from proteins of polymerized cereals of a white almond press cake. The invention also covers the process for obtaining it and the cosmetic compositions.

In cosmetology, numerous attempts have been made to act on the skin so as to obtain a tightening effect. Thus wrinkles and weaknesses of the skin are treated in certain more delicate places so as to counter sagging.

There exist treatments which have long-term effect which act at depths. Such treatments permit compensating the effects of age at the cellular level.

On the other hand, the customers require products permitting having an immediate lifting and smoothing effect. In this case, it is instant results that are sought.

It is known that acting on the skin and producing tension in the skin, at least superficially, leads to results that are clearly visible because the surface condition of the skin is improved.

Thus the color itself is affected because the light is reflected differently relative to a skin that is baggy.

So as to act against loss of regularity of the surface of the skin, the present invention provides an active principle which ensures an immediate tightening effect.

To obtain the envisaged result, there is sought an active principle rich in proteins of high molecular weight, still soluble in water, which is a very useful parameter in the field of cosmetology.

To this end, according to the invention, the process of obtaining an active principle with immediate tightening effect of the skin is characterized in that it comprises the following steps:

dissolution in aqueous phase of a serial press cake, for example Prunus Amygdalus Dulcis, in the amount of 50 to 500 g/l and more particularly 100 to 300 g/l, moderate enzymatic hydrolysis of the solution at an acid pH and at a temperature comprised between 40 and 80° C., separation of the soluble and insoluble phases and inactivation of the medium to interrupt the enzymatic reaction, polymerization of the proteins by addition of a polymerization initiator, separation of the polymerized proteins by filtration, decantation, centrifugation and concentration.

The invention also covers the active principle obtained by the practice of this process, as well as the cosmetic compositions adapted to produce an immediate tightening effect, presented in any suitable galenic form.

The present invention will now be described according to a particular embodiment, by way of the process of obtaining it and the experimental results obtained.

The accompanying sheet of drawings relates to the results obtained with the active principle according to the present invention and permits characterizing the effects. There is also present a curve of results.

The process consists in solubilizing in aqueous phase a white almond press cake in the amount of 50 to 500 g/l and more particularly in the amount of 100 to 300 g/l.

This solution is subjected to acid hydrolysis, at a temperature comprised between 40 and 80° C., in the presence of an enzyme, with a moderate enzymatic action.

Then follows the separation of the soluble and insoluble phases and inactivation of the medium to interrupt the enzymatic action.

An essential step of the process according to the present invention is polymerization of the retained proteins. This step is carried out by addition of a polymerization initiator, in this instance at least 1% of a multifunctional compound such as a polyacid chloride, a polyacid anhydride, a polyisocianate, a polythioisocyanate.

Separation by filtration, centrifugation or decantation permits retaining only the heavy fraction of the proteins thus polymerized, namely the fraction having a molecular weight greater than 600 Kdaltons.

The active principle according to the present invention is characterized by the following data:

1. The weight of dry material is greater than 50 g/l, comprised between 50 and 500 g/l, more particularly between 50 and 250 g/l.

This weight is obtained by passage through an oven at 150° C. until a constant weight is obtained.

2. The pH is comprised between 2.0 and 10.0, particularly between 4.0 and 10.0, more particularly between 7 and 9.

This value is obtained by the potentiometric method, at ambient temperature.

3. The weight of proteins relative to the dry material is greater than 70%.

4. Chromatographic profile:

The molecular weight of the different molecular species is estimated by molecular filtration, by F.P.L.C. (Fast Protein Liquid Chromatography).

The filtration column, of the type sold under the mark "superdex 75" is calibrated with known molecular weight markers such as:

cytochrome C: 12,500 daltons,
bovine albumin: 66,000 daltons,
dehydrogenase alcohol: 150,000 daltons.

The detection of the eluted compounds is carried out in the ultraviolet at 280 nm.

The results are obtained that are indicated in Table 1, FIG. 1, which set forth the characteristics of the obtained active principle.

5. Determination of molecular weight

This determination is carried out by SDS-Page electrophoresis with a 10% polyacrylamide/bisacrylamide gel having a ratio of 36/1.

There are detected two fractions A and B:

Fraction A: Presence of proteins in dimer form with molecular weights from 30 to 50 Kdaltons.

Fraction B: Presence of proteins of very high molecular weights greater than 600 Kdaltons.

The proportion of the two fractions is substantially 50/50.

6. Other parameters:

The obtained active principle is stable at pHs greater than 5, temperature below 50° C. in the presence of ethanol.

So as further to characterize the tightening effect obtained from this active principle for example in an emulsion, carried out on volunteers, there is used as a control means an apparatus commercially known under the name "Cutometer" (Courage and Khazaka).

Such a control means comprises a probe with an opening. This probe is applied to the skin and a constant vacuum is maintained in this probe.

There is measured the depth of penetration of the skin into this probe through the opening, under the effect of vacuum.

The skin, subjected to vacuum, tires more or less quickly and the response time as amplitudes permits determining particularly an instantaneous deformation Ue called the elastic component, and an extensibility Uf.

There it thus carried out on volunteers a first series of applications of the emulsion containing the active principle according to the invention, against a placebo on another predetermined region, for example the face, the arm or the thighs.

A new series of measurements, identical to the first, at the same positions and with the same adjustment of the measuring apparatus, is conducted after a period of 2 hours so as to determine the effect.

The table of FIG. 2 recapitulates the results with increasing percentages of the active principle.

When the instantaneous deformation Ue decreases, the skin is less flexible and hence more tight and if Uf decreases the skin is less extensible and hence also more tight.

It will be seen that 2 hours after isolated application, there is obtained a dose dependent tightening effect which is very interesting and statistically significant and that this effect is also apparent in the different regions studied.

The active principle can be associated with any galenic form: cream, gel, onguent, lotion, milk, emulsion or solution, and with suitable extenders known to those in the art to permit better usage.

There can be cited the following examples of compositions with an active principle having a dry material weight of 121 g/l, a protein quantity of 118 g/l and a pH of 7.8:

1. Composition of gel with tightening effect:
Montanov 202: 3%
Lanol 99: 2%
Lanol 1688: 10%
Active principle according to the present invention: 3%
Sepigel 305: 2%
Preservative: 0.5%
Water qsp: 100

2. Body milk for care of the body for thinning and smoothing:
Lanol 2681: 2%
Lanol 99: 3%
Dc 345: 5%
Glycerol: 2%
Sepigel: 501: 3%
Ethanol: 8%
Preservative: 0.5%
Active thinner: 3%
Active principle according to the invention: 3%
Water qsp: 100

The invention claimed is:

1. A process for obtaining an active principle with immediate skin tightening effect, comprising:
    dissolving in an aqueous phase a white almond press cake 50 to 500 g/l to obtain a mixture;
    moderating enzymatic hydrolysis of said mixture at an acid pH and a temperature comprised between 40 and 80° C., in the presence of an enzyme to obtain a hydrolyzed medium;
    separating soluble and insoluble phases and inactivating the hydrolyzed medium to interrupt the enzymatic reaction;
    polymerizing retained proteins by addition of a polymerization initiator; and
    separating the polymerized proteins as the active principle.

2. The process according to claim 1, wherein the solubilization is carried out in the amount of 100 to 300 g/l of white almond press cake.

3. The process according to claim 1, wherein the white almond press cake is a Prunus Amygdalus Dulcis press cake.

4. The process according to claim 1, wherein the polymerization initiator comprises at least 1% of a compound selected from the group consisting of polyacid chloride, polyacid anhydride, polyisocianate, and polythioisocyanate.

5. The process according to claim 1, wherein the fraction of polymerized proteins has a molecular weight greater than 600 Kdaltons.

6. An active principle obtained by the process according to claim 1, comprising:
    a quantity of dry material from a white almond press cake is between 50 to 500 g/l
    a pH comprised between 2.0 and 10.0; and
    a quantity of proteins relative to the dry material greater than 70%,
    wherein said proteins comprise molecular weight ratio 50/50 of
    i) proteins of dimer form of molecular weight comprised between 30 and 51 Kdaltons; and
    ii) proteins of molecular weight greater than 600 Kdaltons.

7. A process for obtaining an active principle with immediate skin tightening effect, comprising:
    dissolving a white almond press cake in an aqueous phase to obtain a mixture;
    enzymatically hydrolyzing said mixture at an acid pH to obtain a hydrolyzed medium;
    separating soluble and insoluble phases and inactivating the hydrolyzed medium to interrupt the enzymatic reaction;
    polymerizing retained proteins by addition of a polymerization initiator; and
    separating the polymerized proteins to obtain said active princple.

8. The process according to claim 7, wherein the solubilization is carried out in the amount of 50 to 500 g/l of white almond press cake.

9. The process according to claim 7, wherein the white almond press cake is a Prunus Amygdalus Dulcis press cake.

10. The process according to claim 7, wherein the polymerization initiator comprises at least 1% of a multifunctional compound selected from the group consisting of polyacid chloride, polyacid anhydride, polyisocianate, and polylthioisocyanate.

11. The process according to claim 7, wherein the fraction of polymerized proteins has a molecular weight greater than 600 Kdaltons.

12. An active principle, obtained by the process according to claim 7 comprising:
    a quantity of dry material from a white almond press cake;
    a pH comprised between 2.0 and 10.0; and
    a quantity of proteins relative to the dry material greater than 70%,
    wherein said proteins comprise
    i) proteins in a dimer form with a molecular weight between 30 and 51 Kdaltons; and
    ii) proteins with a high molecular weight greater than 600 Kdaltons.

* * * * *